United States Patent [19]

Okaniwa et al.

[11] Patent Number: 4,594,224

[45] Date of Patent: Jun. 10, 1986

[54] ANALYTICAL ELEMENT

[75] Inventors: Kenichiro Okaniwa; Shozo Kikugawa; Mikio Koyama, all of Hino, Japan

[73] Assignee: Konishiroku Photo Industry Co., Ltd., Tokyo, Japan

[21] Appl. No.: 597,818

[22] Filed: Apr. 9, 1984

Related U.S. Application Data

[63] Continuation of Ser. No. 343,354, Jan. 27, 1982, abandoned.

[30] Foreign Application Priority Data

Jan. 30, 1981 [JP] Japan ................................ 56-13203

[51] Int. Cl.[4] ...................... G01N 21/78; G01N 33/52
[52] U.S. Cl. ........................................ 422/56; 422/57; 435/805
[58] Field of Search .................... 422/55–58; 435/805

[56] References Cited

U.S. PATENT DOCUMENTS

| | | | |
|---|---|---|---|
| 3,061,523 | 10/1962 | Free | 435/14 |
| 3,897,214 | 7/1975 | Lange et al. | 422/56 |
| 4,050,898 | 9/1977 | Goffe et al. | 422/57 |
| 4,144,306 | 3/1979 | Figueras | 422/56 |
| 4,258,001 | 3/1981 | Pierce et al. | 435/7 X |
| 4,292,272 | 9/1981 | Kitajima et al. | 422/56 X |
| 4,427,632 | 1/1984 | Okaniwa et al. | 422/56 |

OTHER PUBLICATIONS

"The Condensed Chemical Dictionary", Hawley, Tenth Edition, Van Nostrand Reinhold Co., 1981, p. 97.

*Primary Examiner*—Arnold Turk
*Attorney, Agent, or Firm*—Frishauf, Holtz, Goodman & Woodward

[57] ABSTRACT

There is presented an improved simple quantitative analytical element for analysis of components in a body fluid such as blood, having a reagent layer constituted of a hydrophilic colloid containing at least one reagent reactive with a component in a liquid sample provided on a support, and also a development layer of a fibrous structure on the reagent layer on the opposite side to the support. A liquid sample can be distributed uniformly through the reagent layer to enable quantitative analysis.

15 Claims, No Drawings

ANALYTICAL ELEMENT

This application is a continuation of application Ser. No. 343,354, filed Jan. 27, 1982 now abandoned.

This invention relates to an improved simple quantitative analytical element for analysis of contents in a body fluid.

There have been developed a large number of methods for analysis of test components in testing of a liquid. These methods may be classified broadly into the reaction system in liquid and the reaction system in solid.

The analytical reaction in a solution system (hereinafter referred to as "wet chemistry") includes a large number of procedures, varying widely from an analytical procedure of so called manual method in which no machine is used at all to automatic quantitative analyzer frequently used in recent years in clinical diagnostic laboratories.

Among them, automatic quantitative analyzers are useful especially for analysis of blood. They are analytical systems based on continuous flow analysis, using various methods in which a sample, a diluent and analytical reagent(s) are mixed together and fed into an analyzer.

However, these continuous analyzers, as disclosed in U.S. Pat. No. 2,797,149, are complicated and expensive, requiring operational technique by an expert. Repeated washing operations are also necessarily required to be performed, for which enormous amounts of time and labor are consumed. In addition, waste liquors from such washings will inevitably cause the problem of environmental pollution.

On the other hand, there have been widely employed the analytical methods in which the dry system reaction (hereinafter referred to as "dry chemistry") is used. They are provided generally in the form of a filter paper etc. impregnated with a reagent. These may frequently be called as "dip and read system" or "dip, wipe and read system", depending on the type of the reaction procedure, but there is no great difference between these modes.

The test papers as mentioned above may be prepared by impregnating a carrier such as a filter paper with a reagent solution followed by drying, as disclosed in U.S. Pat. Nos. 3,050,373 or 3,061,523. They are generally called as enzyme test papers or test strips, and measurement may be performed by adding dropwise a sample on such a test strip or by dipping a test strip in a sample solution and then observing the change in color or in concentration with the naked eye or by a reflectometer.

Various improvements have been attempted for test papers employing dry chemistry.

For example, as disclosed in Japanese Patent Publication No. 39558/1975, a filter paper is impregnated with a reagent and then a semi-permeable substance such as ethyl cellulose is covered on the fibers of the filter paper thereby to shield the test paper from contact with excessive oxygen in the air, thus resulting in prevention of undesirable color formation as well as in prevention of excessive take-up of the sample. Further, as disclosed in Japanese Patent Publication No. 6551/1978, a fine mesh such as transparent web or fabric is covered on a filter paper impregnated with a reagent to aid in permeation of a sample uniformly into the filter paper, prevent excessive holding of a sample and also prevent contamination on the filter surface by contact during operation.

These test papers are useful since they are simple in handling and can give results immediately. However, the test papers having carriers such as filter paper impregnated with reagents are also known to involve a number of drawbacks.

That is, non-uniform test results known as "banding" are liable to occur when samples are supplied onto filter papers. This may be caused by undesirable diffusion of a reagent or a sample to be analyzed formed in a carrier such as filter paper, which is in turn chromatographed through the carrier.

When such a phenomenon occurs, local intensification of density will be caused in color formation during quantitative analytical reaction to give scattered test results. Thus, such a carrier as a filter paper conventionally proposed to be a desirable matrix material for dry chemistry involves a number of drawbacks such as chromatographic effect of sample components due to chemical properties of said carrier, physical suppression, non-uniform capillary migration of sample components or occurrence of other non-uniform permeation.

For the reasons mentioned above, the so called test papers have been utilized but in the field of qualitative or semiquantitative analysis.

The object of the present invention is to provide an analytical element having excellent quantitative characteristics without need of skilled operational technique.

The present inventors have made extensive studies and consequently have overcome the above drawbacks by use of an analytical element having the constitution as specified below.

That is, the analytical element according to the present invention comprises a light-transmissive and liquid-impervious support, at least one reagent layer constituted of a hydrophilic colloid containing at least one reagent which reacts with a component in a liquid sample and at least one development layer of a fibrous structure provided at a position on the reagent layer on the opposite side to that of said support for permitting the component in said liquid sample to permeate into said reagent layer, said development layer of a fibrous structure being formed by coating of a dispersion of fibers.

The analytical element according to the present invention is to be described in detail below.

First, the aforesaid liquid-impervious, light-transmissive support according to the analytical element of the present invention (hereinafter abridged as the support according to the present invention) may be any kind of support, so long as it is impervious to liquids and light-transmissive. For example, various polymeric materials such as cellulose acetate, polyethylene terephthalate, polycarbonate or polystyrene are suitable for this purpose. In this case, the above support may have a thickness which can freely be selected, but preferably in the range of from about 50 microns to 250 microns. The one side surface on the observation side of the support according to the present invention may also be freely worked depending on the purpose intended. Next, when the aforesaid reagent layer according to the present invention is provided on the above support, it may be coated directly on the support, but in some cases, a light-transmissive primer coating may also be used to effectively enhance adhesion between the reagent layer and the support.

The above reagent layer according to the present invention is used to incorporate reagents for carrying out quantitative reaction with the test components to be analyzed and to permit the quantitative reaction in said layer.

And, since the above reagent layer is provided as a layer by coating on the support using a hydrophilic colloid as medium, it can contain uniformly reagents, as different from the test paper of prior art having a filter paper impregnated with reagents, and the contents of the reagents can advantageously freely be controlled. As the hydrophilic colloidal substance to be used in such a reagent layer according to the present invention, there may preferably be used natural or synthetic macromolecular substances, more preferably gelatin, gelatin derivatives such as modified gelatin, polyvinyl alcohol, polyvinyl pyrrolidone, etc. Among them, as the particularly preferred hydrophilic colloidal substances, there may be mentioned gelatin derivatives such as gelatin.

These hydrophilic colloidal substances may preferably have a degree of swelling of about 150 to about 500% and a film thickness, which may be selected as desired but required to be at least about 5 microns.

The reagents to be incorporated in the reagent layer formed as described above are of course determined depending on the test components to be analyzed in a sample and the analytical reaction selected for analysis of the components. When the analytical reaction is constituted to include two or more kinds of reagents, these reagents may either be mixed to be incorporated in the same reagent layer or respectively in separate layers. Such a selection may sometimes be determined depending on the mechanism of the analytical reaction per se and any desired constitution may be employed, so long as it has no undesirable influence.

On the other hand, it is also possible to carry out the reaction between two or more kinds of test components in a sample in the same reagent layer. In this case, it is required that the two or more analytical reactions may not interfere with each other and also that the analytical reactions should be selected so as to avoid mutual influence during measurement of the reaction products formed.

The thus constituted reagent layer may be coated generally by a coating method on the support according to the present invention. But, as mentioned above, there may also be provided various kinds of layers, except for those unsuitable for the object of the present invention, between the reagent layer and the support.

The development layer of a fibrous structure according to the present invention may be provided as a single layer or plural layers directly or indirectly on the reagent layer previously provided on the support.

The development layer of a fibrous structure is provided for the purposes as mentioned below:

(1) To distribute a constant volume of a liquid sample uniformly to a constant volume per unit area through the reagent layer;

(2) To remove substances or factors which interfere with the analytical reactions in the liquid sample;

(3) To effect a background action which reflects the measured light transmitted through the support during spectrophotometric analysis.

Accordingly, the development layer of a fibrous structure can perform all the three functions as mentioned above, but the three functions may also suitably be separated by use of the layers having respective functions.

Further, it is also possible to use a layer having two of the three functions and a layer having the other remaining function.

The development layer of a fibrous structure according to the present invention may have a thickness which may freely be selected depending on the purpose, but preferably about 30 microns to about 600 microns, more preferably about 50 microns to about 400 microns.

And, the development layer of a fibrous structure according to the present invention as mentioned above does not assume a structure like mesh or fabric as disclosed in Japanese Patent Publication No. 6551/1978 or Japanese Provisional Patent Publication No. 164356/1980, and its free pore area is of course substantially zero.

As the material for forming the development layer of a fibrous structure according to the present invention, there may be employed natural celluloses, derivatives thereof, and synthetic fibers such as polyethylene, polypropylene, polyamide, etc. Said layer may be constituted of three-dimensional random entanglements of various fibers, irrespective of whether they are natural or synthetic.

Further, as the material for forming the above development layer of a fibrous structure, there may be selected single or plural kinds of materials with any desired size, which is 50 to 325 mesh, preferably 100 to 320 mesh, more preferably 200 to 300 mesh.

The development layer of a fibrous structure according to the present invention may be prepared by coating according to various methods. One exemplary method is mentioned below.

That is, the fibers of the present invention are dispersed in a liquid carrier which does not dissolve said fiber to prepare a dispersion of said fibers, which stable dispersion is then applied on a support, followed by removal of the liquid carrier while forming said fibrous structure.

A dispersion useful for preparation of the development layer of a fibrous structure is required to be stable for a time sufficient to apply said dispersion on a support.

For preparation of such a stable dispersion, it is possible to use various methods singly or in combination. For example, one useful method comprises adding a surfactant and a polymer into a liquid carrier as an accelerator or a binder useful for distribution or stabilization in the fiber dispersion.

As useful surfactants, there may be employed all surfactants of either ionic(anionic or cationic) or nonionic, but nonionic surfactants are more effective. Examples of nonionic surfactants are polyalkylene-glycol derivatives of alkyl-substituted phenols such as 2,5-di-t-butylphenoxy polyethyleneglycol, p-octylphenoxy polyglycidylether, p-isononylphenoxy polyethylene glycol, and polyalkylene glycol esters of higher fatty acids. These surfactants have the effect of controlling the permeation speed of a liquid sample into the development layer of a fibrous structure simultaneously with the effect of inhibiting generation of undesirable "chromatography phenomenon". Further, as the effect of a surfactant, there is also the effect of alleviating various undesirable influences by proteins contained in a biological sample.

The above surfactant may be employed in an amount which can be widely varied, but generally in an amount of 10 to 0.005% by weight based on the weight of the fibers, preferably 6 to 0.05% by weight. Further, as an alternative method, there may be employed sonication treatment, physical mixing, and physical stirring treatment and pH adjustment of said fibers and liquid carrier.

These methods can be more effective by combination with the aforesaid method.

The aforesaid liquid carrier employed may be an aqueous liquid. But, there may also be employed other liquid carriers such as various organic liquids provided that said fibers are insoluble in such carriers and therefore the characteristics of the fibrous structure can be maintained.

Typical liquid carriers other than water may include organic solvents miscible with water, aqueous solutions of water with organic solvents miscible with water and suitable organic solvents immiscible with water. Organic solvents miscible with water may be exemplified by lower alcohols (namely, alcohols with alkyl moieties having 1 to 4 carbon atoms), acetone and tetrahydrofuran. Solvents immiscible with water may be inclusive of lower alkyl esters such as ethyl acetate and halogenated organic solvents such as halogenated hydrocarbons (e.g. chloroform, methyl chloride and carbon tetrachloride).

Further, the aforesaid polymer is useful not only for stabilization of the aforesaid dispersion, but also useful as a binder at the time of formation of the fibrous structure of the present invention, and it is possible to use various natural or synthetic polymers.

As preferred polymers to be employed, there may be mentioned, for example, gelatin, gelatin derivatives such as modified gelatin, polyvinyl alcohol, polyvinyl pyrrolidone, polycarbonate, polyamide, cellulose acetate, polyvinyl butyral, etc.

The above polymer may be used in an amount which can be selected from a wide range, but preferably in an amount such that substantial portions of the void volume formed by three-dimensional entanglements may not be filled therewith, namely 10 to 0.005% by weight, more preferably 6 to 0.05% by weight, based on the weight of the fibers.

The analytical element including the above development layer of a fibrous structure can take any desired arrangement, and may also have one or more of the development layer of a fibrous structure of the present invention. Further, it is also possible to constitute the analytical element in conformity with the object of the present invention by combining the development layer of a fibrous structure of the present invention optionally with various functional layers, reagent containing members, as exemplified by the reagent layer, filtration layer, reflection layer, undercoating layer as disclosed in U.S. Pat. No. 3,992,158, radiation blocking layer as disclosed in U.S. Pat. No. 4,042,335, buyer layer as disclosed in U.S. Pat. No. 4,066,403, registration layer as disclosed in U.S. Pat. No. 4,144,306, migration inhibition layer as disclosed in U.S. Pat. No. 4,166,093, scintillation layer as disclosed in U.S. Pat. No. 4,127,499, scavenging layer as disclosed in Japanese Provisional Patent Publication No. 90859/1980 and destructive pod-like member as disclosed in U.S. Pat. No. 4,110,079, and the like.

Further, the analytical element having the development layer of a fibrous structure according to the present invention can be subjected to so called "calendering treatment" by passing through a pair of pressure rollers to be increased in smoothness on the surface of said development layer, whereby favorable result can be obtained in respect of optical reflection.

The analytical element of the present invention having the constitution as described above can accomplish its object by supplying a liquid sample from the side of the development layer of a fibrous structure and then observing the analytical reaction from the side of the transparent support.

A liquid sample to be applied to the analytical element according to the present invention may be used in an amount as desired, but preferably in an amount of about 50 $\mu$l to about 5 $\mu$l, more preferably about 20 $\mu$l to about 5 $\mu$l. Usually, it is preferred to use about 10 $\mu$l of a liquid sample.

The analytical reaction to be employed for the analytical element of the present invention may be determined suitably depending on the purpose of analysis. For example, it may be used for analysis of biological liquid samples such as blood or components in urine.

These can be constituted easily by suitable selection of analytical reagents so as to be available for analysis of a number of components, including glucose, urea nitrogen, ammonia, uric acid, cholesterol, triglyceride, creatine, creatinine, bilirubin and others.

Measurement of such an analytical reaction may be performed according to the method suitably selected depending on the analytical reaction employed, but it is generally practiced by spectrophotometric analysis at the visible region.

It is also possible, however, to employ fluorophotometry or ultraviolet spectrophotometry depending on the analytical reaction selected.

For example, when an enzyme which hydrolyzes glucose (glucose oxidase), peroxidase, 4-aminoantipyrine hydrochloride and 7-hydroxy-1-naphthol are incorporated in a reagent layer, and glucose is decomposed into gluconic acid and hydrogen peroxide and the hydrogen peroxide is then decomposed by peroxidase, 4-aminoantipyrine hydrochloride and 7-hydroxy-1-naphthol undergo coupling to form a dyestuff. Glucose can be determined by measurement of the concentration of the dyestuff.

The analytical element of the present invention, which has the constitution as described in detail above, is free from generation of non-uniform concentration of reagents or chromatography phenomenon and can be used for simpler and more rapid quantitative analysis of components in liquid samples, particularly a biological liquid sample, by means of a conventional spectro-photometer.

Further, formation of the development layer of a fibrous structure is possible only by coating and drying, and the coating conditions and the drying conditions are not particularly limited. Thus, the present invention has a practical advantage of very easy preparation.

The present invention is further illustrated by referring to the following Examples, by which the embodiments of the present invention are not limited.

EXAMPLE 1

On a transparent polyethylene terephthalate support of a thickness of 180 $\mu$m, there was coated 216 mg/dm$^2$ of a deionized gelatin (dry film thickness=about 20 $\mu$m) and each of fiber dispersions I–III having the compositions as shown in Table 1 was coated thereon to prepare Sample-I, II and III of the present invention.

TABLE 1

| Sample No. | Dispersion No. | Fiber dispersion Compositon of dispersion | | | |
|---|---|---|---|---|---|
| | | Fiber | Solvent | Polymer | Surfactant |
| Sample-I | Dispersion-I | F-1 8.3 g | Water 45 g | Polyvinyl pyrroli- | — |

TABLE 1-continued

| Sample No. | Dispersion No. | Fiber dispersion | | | |
|---|---|---|---|---|---|
| | | Compositon of dispersion | | | |
| | | Fiber | Solvent | Polymer | Surfactant |
| Sample-II | Dispersion-II | F-1 8.3 g | Water 50 g | done (K-90) 0.4 g Poly-vinyl pyrroli-done (K-90) 0.4 g | SA 0.5 g |
| Sample-III | Dispersion-III | F-2 8.3 g | Water 60 g | — | — |

In the above Table,

F-1 is Filter Powder C (Toyo Roshi K.K.),

F-2 is Filter Powder A (Toyo Roshi K.K.),

SA represents p-nonylphenoxy poly(ethylene oxide). On the other hand, as a Comparative Sample, a filter paper (Toyo Roshi K.K. No. 7) was adhered directly on a transparent polyethylene terephthalate support with a thickness of 180 μm to provide Comparative Sample (I), and the same filter paper was adhered after impregnation of the same support with 5% aqueous gelatin solution and drying thereof to provide Comparative Sample (II).

These Samples (I), (II), (III) and Comparative Samples (I), (II) were added dropwise with 10 μl of an aqueous solution of a red dyestuff Brilliant Scarlet 3R and spot diameters were measured 7 minutes later from the side of the support.

The reflection densities were also measured (by Sakura photoelectric densitometer PAD-60 Model, produced by Konishiroku Photo Industry Co., Ltd.) using a green ($\lambda_{max}$=546 nm) filter to determine the difference ΔD between the maximum density and the minimum density in the spot. Measurement was repeated 10 times for each of the Samples and Comparative Samples, and the maximum, minimum and average values are shown together with the maximum ΔD within ten measurements.

The results are shown in Table 2 below.

TABLE 2

| | Spot diameter (mm) | | | |
|---|---|---|---|---|
| | Max. | Min. | Aver. | ΔD |
| Comparative sample (I) | 16.1 | 10.3 | 13.3 | 0.21 |
| Comparative sample (II) | 16.4 | 9.1 | 12.7 | 0.24 |
| Sample of the invention (I) | 10.5 | 10.0 | 10.1 | 0.02 |
| Sample of the invention (II) | 10.1 | 10.0 | 10.0 | 0.01 |
| Sample of the invention (III) | 11.1 | 10.5 | 11.1 | 0.04 |

As apparently seen from the above Table 2, no scattering of values of spot diameters can be seen and the density distribution within the coloration region is very small.

On the other hand, in Comparative samples, not only the spot diameter values are scattered widely, but also the scattering of the densities within the coloration region is also great.

EXAMPLE 2

On a transparent, 180 μm thick polyethylene terephthalate support, the following layers were coated:

Reagent layer (thickness of dried film=about 20 μm) containing the following components:

| Deionized gelatin | 216 mg/dm² |
|---|---|
| 1,7-Dihydroxynaphthalene | 6.56 mg/dm² |
| 4-Aminoantipyrine hydrochloride | 8.6 mg/dm² |
| Dimedone | 2.16 mg/dm² |
| Glucose oxidase | 244 unit/dm² |
| Peroxidase | 100 unit/dm² |
| 3,3-Dimethylglutaric acid | 19.6 mg/dm² |

On the above reagent layer, the dispersion-II as used in Example 1 was coated and dried to prepare an analytical element for analysis of glucose. On this analytical element, aqueous glucose solution with various concentration of 100 mg/dl, 150 mg/dl, 200 mg/dl, 250 mg/dl, 300 mg/dl and 350 mg/dl and artificial serums containing the same levels of glucose were each added dropwise in quantity of 10 μl. After incubation at 37° C. for 7 minutes, the density of the reddish brown dyestuff formed was measured at the wavelength of 490 nm, whereby it was found that the glucose concentration was in direct proportion to the reflection density.

What we claim is:

1. An analytical element, comprising a light-transmissive and liquid-impervious support, at least one reagent layer comprising a hydrophilic colloid containing at least one reagent which reacts with a component in a liquid sample, and at least one development layer having a fibrous structure provided at a position on a side of the reagent layer opposite to that of said support for permitting the component in said liquid sample to permeate into said reagent layer, said development layer having a fibrous structure being formed by coating said reagent layer with a dispersion of fibers wherein said fibers have a size of 50 to 325 mesh.

2. The analytical element of claim 1 wherein the development layer has a thickness of from 30 to 600 microns.

3. The analytical element of claim 1 wherein the support comprises a polymeric material selected from the group consisting of cellulose acetate, polyethylene terephthalate, polycarbonate and polystyrene.

4. The analytical element of claim 3 wherein the support has a thickness of from 50 to 250 microns.

5. The analytical element of claim 1 wherein the hydrophilic colloid is selected from the group consisting of gelatin, gelatin derivatives, polyvinyl alcohol and polyvinyl pyrrolidone.

6. The analytical element of claim 5 wherein the hydrophilic colloid is gelatin.

7. The analytical element of claim 5 wherein the hydrophilic colloid is in the form of a film having a thickness of at least 5 microns.

8. The analytical element of claim 1 wherein the dispersion of fibers is an aqueous dispersion of natural or synthetic fibers.

9. The analytical element of claim 8 wherein said fibers are selected from the group consisting of natural cellulose and derivatives thereof, polyethylene, polypropylene and polyamide.

10. The analytical element of claim 8 wherein the dispersion contains a surfactant.

11. The analytical element of claim 10 wherein the dispersion further contains a polymer binder.

12. The analytical element of claim 10 wherein the amount of said surfactant is from 0.005 to 10% by weight based on the weight of said fibers.

13. The analytical element of claim 10 wherein the surfactant is a nonionic surfactant.

14. The analytical element of claim 13 wherein the dispersion further contains a polymer binder.

15. An analytical element comprising a light-transmissive and liquid-impervious support, at least one reagent layer comprising a hydrophilic colloid selected from the group consisting of gelatin, gelatin derivatives, polyvinyl alcohol and polyvinyl pyrrolidone, having a thickness of at least 5 microns, and at least one reagent which reacts with a component in a liquid sample, and at least one development layer having a fibrous structure, the fibers of said fibrous structure having a size of 50 to 325 mesh and being selected from natural cellulose and derivatives thereof, polyethylene, polypropylene and polyamide, said development layer being provided at a position on a side of the reagent layer opposite to that of said support for permitting the component in said liquid sample to permeate into said reagent layer, said development layer being formed by coating said reagent layer with a dispersion comprising and fibers and a surfactant.

* * * * *